(12) United States Patent
Sakai et al.

(10) Patent No.: US 8,940,738 B2
(45) Date of Patent: Jan. 27, 2015

(54) PYRIMIDONE COMPOUNDS

(75) Inventors: Daiki Sakai, Kanagawa (JP); Kazuki Nakayama, Tokyo (JP); Kazutoshi Watanabe, Tokyo (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 11 days.

(21) Appl. No.: 13/389,504

(22) PCT Filed: Aug. 11, 2010

(86) PCT No.: PCT/JP2010/063890
§ 371 (c)(1),
(2), (4) Date: Apr. 24, 2012

(87) PCT Pub. No.: WO2011/019089
PCT Pub. Date: Feb. 17, 2011

(65) Prior Publication Data
US 2012/0220591 A1 Aug. 30, 2012

(30) Foreign Application Priority Data
Aug. 13, 2009 (JP) ................. 2009-204095

(51) Int. Cl.
| | | |
|---|---|---|
| A61K 31/5377 | (2006.01) |
| A61P 25/28 | (2006.01) |
| A61P 9/10 | (2006.01) |
| C07D 413/04 | (2006.01) |
| C07D 401/04 | (2006.01) |
| C07D 413/14 | (2006.01) |

(52) U.S. Cl.
CPC ............ *C07D 413/04* (2013.01); *C07D 401/04* (2013.01); *C07D 413/14* (2013.01)
USPC ...................... 514/236.2; 544/123; 514/235.8

(58) Field of Classification Search
CPC ............. A61K 31/535; A61K 31/5377; C07D 413/04; C07D 413/06; C07D 413/14
See application file for complete search history.

(56) References Cited

U.S. PATENT DOCUMENTS

| | | |
|---|---|---|
| 7,504,411 B2 | 3/2009 | Watanabe et al. |
| 7,994,315 B2 | 8/2011 | Okuyama et al. |
| 2005/0130967 A1 | 6/2005 | Uehara et al. |
| 2009/0124618 A1 | 5/2009 | Watanabe et al. |
| 2009/0233918 A1 | 9/2009 | Fukunaga et al. |
| 2010/0113775 A1 | 5/2010 | Watanabe et al. |
| 2011/0021773 A1 | 1/2011 | Fukunaga et al. |
| 2011/0251385 A1 | 10/2011 | Okuyama et al. |
| 2011/0257392 A1 | 10/2011 | Okuyama et al. |
| 2012/0095216 A1 | 4/2012 | Watanabe et al. |

FOREIGN PATENT DOCUMENTS

| | | |
|---|---|---|
| EP | 0 616 032 B1 | 11/2003 |
| JP | 2008-512347 | 4/2008 |
| WO | 01/70729 A1 | 9/2001 |
| WO | 03/027080 A1 | 4/2003 |
| WO | 03/037888 A1 | 5/2003 |
| WO | 2004/085408 A1 | 10/2004 |
| WO | 2006/028290 A1 | 3/2006 |
| WO | 2007/011065 A2 | 1/2007 |
| WO | 2007/119463 A1 | 10/2007 |
| WO | 2008/023239 A1 | 2/2008 |
| WO | 2008/078837 A1 | 7/2008 |
| WO | 2009/035159 | 3/2009 |
| WO | 2009/035162 | 3/2009 |

OTHER PUBLICATIONS

Simone, Oncology: Introduction, Cecil Textbook of Medicine, 20th Edition, 1996 vol. 1, pp. 1004-1010.*
Ferrer et al., "Glycogen synthase kinase-3 is associated with neuronal and glial hyperphosphorylated tau deposits in Alzheimer's disease, Pick's disease, progressive supranuclear palsy and corticobasal degeneration", Acta Neuropathol., vol. 104, pp. 583-591 (2002).
Koh et al., "Role of GSK-3β activity in motor neuronal cell death induced by G93A or A4V mutant hSOD1 gene", European Journal of Neuroscience, vol. 22, pp. 301-309 (2005).

(Continued)

*Primary Examiner* — San-Ming Hui
*Assistant Examiner* — Andrew Lee
(74) *Attorney, Agent, or Firm* — Greenblum & Bernstein, P.L.C.

(57) ABSTRACT

A pyrimidone derivative represented by general formula (I) or a pharmaceutically acceptable salt thereof:

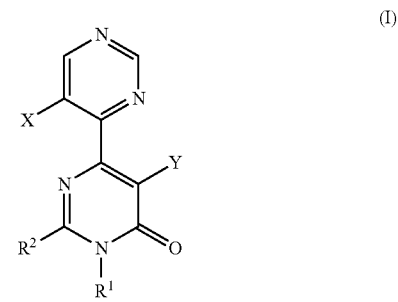

wherein X represents hydrogen atom and Y represents hydroxyl group, or X represents fluorine atom and Y represents hydrogen atom; $R^1$ represents a $C_{1-6}$ alkyl group; $R^2$ represents a morpholin-4-yl group which may be substituted, or the like, which is used for preventive and/or therapeutic treatment of a disease caused by tau protein kinase 1 hyperactivity such as a neurodegenerative diseases (e.g. Alzheimer disease).

5 Claims, No Drawings

(56) References Cited

OTHER PUBLICATIONS

Droucheau et al., "Plasmodium falciparum glycogen synthase kinase-3: molecular model, expression, intracellular localisation and selective inhibitors", Biochimica Et Biophysica Acta, vol. 1697, pp. 181-196 (2004).

Frame et al., "GSK3 takes centre stage more than 20 years after its discovery", Biochem. J., vol. 359, pp. 1-16 (2001).

Eldar-Finkelman, "Glycogen synthase kinase 3: an emerging therapeutic target", Trends in Molecular Medicine, vol. 8, No. 3, pp. 126-132 (2002).

Kaytor et al., "The GSK3β signaling cascade and neurodegenerative disease", Current Opinion in Neurobiology, vol. 12, pp. 275-278 (2002).

Masters et al., "Neuronal origin of a cerebral amyloid: neurofibrillary tangles of Alzheimer's disease contain the same protein as the amyloid of plaque cores and blood vessels", The EMBO Journal, vol. 4, No. 11, pp. 2757-2763 (1985).

Glenner et al., "Alzheimer's Disease: Initial Report of the Purification and Characterization of a Novel Cerebrovascular Amyloid Protein", Biochemical and Biophysical Research Communications, vol. 120, No. 3, pp. 885-890 (1984).

Masters et al., "Amyloid plaque core protein in Alzheimer disease and Down syndrome", Proc. Natl. Acad. Sci. USA, vol. 82, pp. 4245-4249 (1985).

Wischik et al., "Isolation of a fragment of tau derived from the core of the paired helical filament of Alzheimer disease", Proc. Natl. Acad. Sci. USA, vol. 85, pp. 4506-4510 (1988).

Kondo et al., "The Carboxyl Third of Tau is Tightly Bound to Paired Helical Filaments", NEURON, vol. 1, pp. 827-834 (1988).

Sherrington et al., "Cloning of a gene bearing missense mutations in early-onset familial Alzheimer's disease", Nature, vol. 375, pp. 754-760 (1995).

Levy-Lahad et al., "Candidate Gene for the Chromosome 1 Familial Alzheimer's Disease Locus", Science, vol. 269, pp. 973-977 (1995).

Rogaev et al., "Familial Alzheimer's disease in kindreds with missense mutations in gene on chromosome 1 related to the Alzheimer's disease type 3 gene", Nature, vol. 376, pp. 775-778 (1995).

Borchelt et al., "Familial Alzheimer's Disease-Linked Presenilin 1 Variants Elevate Aβ1-42/1-40 Ratio In Vitro and In Vivo", Neuron, vol. 17, pp. 1005-1013 (1996).

Tomita et al., "The presenilin 2 mutation (N141I) linked to familial Alzheimer disease (Volga German families) increases the secretion of amyloid β protein ending at the 42nd (or 43rd) residue", Proc. Natl. Acad. Sci. USA, vol. 94, pp. 2025-2030 (1997).

Copani et al., "β-Amyloid Protein Potentiates Injury by Glucose Deprivation in Neuronal Cortical Cultures ", Society for Neuroscience Abstracts, vol. 17, pp. 1445 (1991).

Siman et al., "Proteolytic Processing of β-Amyloid Precursor by Calpain I", The Journal of Neuroscience, vol. 10, No. 7, pp. 2400-2411 (1990).

Ihara et al., "Phosphorylated Tau Protein is integrated into Paired Helical Filaments in Alzheimer's Disease", J. Biochem., vol. 99, No. 6, pp. 1807-1810 (1986).

Grundke-Iqbal et al., "Abnormal phosphorylation of the microtubule-associated protein (tau) in Alzheimer cytoskeletal pathology", Proc. Natl. Acad. Sci. USA, vol. 83, pp. 4913-4917 (1986).

Ishiguro et al., "Tau Protein Kinase I Converts Normal Tau Protein into A68-like Component of Paired Helical Filaments", The Journal of Biological Chemistry, vol. 267, No. 16, pp. 10897-10901 (1992).

Ishiguro et al., "Glycogen synthase kinase 3β is identical to tau protein kinase I generating several epitopes of paired helical filaments", FEBS Letters, vol. 325, No. 3, pp. 167-172 (1993).

Yankner et al., "Neurotrophic and Neurotoxic Effects of Amyloid β Protein: Reversal by Tachykinin Neuropeptides", Science, vol. 250, pp. 279-282 (1990).

Takashima et al., "Tau protein kinase I is essential for amyloid β-protein-induced neurotoxicity", Proc. Natl. Acad. Sci. USA, vol. 90, pp. 7789-7793 (1993).

English Translation of International Search Report issued with respect to PCT/JP2010/063890, dated Oct. 20, 2010.

English Translation of International Preliminary Report on Patentability issued with respect to PCT/JP2010/063890, dated Feb. 14, 2012.

U.S. Appl. No. 13/389,512 to Kazuki Nakayama et al., which was filed on Feb. 8, 2012.

Office Action issued with respect to European Patent Application No. 10748155.8, dated Mar. 22, 2013.

Japanese Office Action issued with respect to Japanese Patent Application No. 2012-507487, mailed Aug. 27, 2013, along with an English language excerption.

* cited by examiner

PYRIMIDONE COMPOUNDS

TECHNICAL FIELD

The present invention relates to compounds that are useful as an active ingredient of a medicament for preventive and/or therapeutic treatment of diseases mainly caused by abnormal activity of tau protein kinase 1 (TPK1 also called GSK3beta: glycogen synthase kinase 3 beta), such as neurodegenerative diseases (e.g. Alzheimer disease).

BACKGROUND ART

Alzheimer disease is progressive senile dementia, in which marked cerebral cortical atrophy is observed due to degeneration of nerve cells and decrease of nerve cell number. Pathologically, numerous senile plaques and neurofibrillary tangles are observed in brain. The number of patients has been increased with the increment of aged population, and the disease arises a serious social problem. Although various theories have been proposed, a cause of the disease has not yet been elucidated. Early resolution of the cause has been desired.

It has been known that the degree of appearance of two characteristic pathological changes of Alzheimer disease well correlates to the degree of intellectual dysfunction. Therefore, researches have been conducted from early 1980's to reveal the cause of the disease through molecular level investigations of components of the two pathological changes. Senile plaques accumulate extracellularly, and β amyloid protein has been elucidated as their main component (abbreviated as "A β" hereinafter in the specification: Biochem. Biophys. Res. Commun., 120, 885 (1984); EMBO J., 4, 2757 (1985); Proc. Natl. Acad. Sci. USA, 82, 4245 (1985)). In the other pathological change, i.e., the neurofibrillary tangles, a double-helical filamentous substance called paired helical filament (abbreviated as "PHF" hereinafter in the specification) accumulate intracellularly, and tau protein, which is a kind of microtubule-associated protein specific for brain, has been revealed as its main component (Proc. Natl. Acad. Sci. USA, 85, 4506 (1988); Neuron, 1, 827 (1988)).

Furthermore, on the basis of genetic investigations, presenilins 1 and 2 were found as causative genes of familial Alzheimer disease (Nature, 375, 754 (1995); Science, 269, 973 (1995); Nature. 376, 775 (1995)), and it has been revealed that presence of mutants of presenilins 1 and 2 promotes the secretion of A β (Neuron, 17, 1005 (1996); Proc. Natl. Acad. Sci. USA, 94, 2025 (1997)). From these results, it is considered that, in Alzheimer disease, A β abnormally accumulates and agglomerates due to a certain reason, which engages with the formation of PHF to cause death of nerve cells. It is also expected that extracellular outflow of glutamic acid and activation of glutamate receptor responding to the outflow may possibly be important factors in an early process of the nerve cell death caused by ischemic cerebrovascular accidents.

It has been reported that kainic acid treatment that stimulates the AMPA receptor, one of glutamate receptor, increases mRNA of the amyloid precursor protein (abbreviated as "APP" hereinafter in the specification) as a precursor of A β (Society for Neuroscience Abstracts, 17, 1445 (1991)), and also promotes metabolism of APP (The Journal of Neuroscience, 10, 2400 (1990)). Therefore, it has been strongly suggested that the accumulation of A β is involved in cellular death due to ischemic cerebrovascular disorders. Other diseases in which abnormal accumulation and agglomeration of A β are observed include, for example, Down syndrome, cerebral bleeding due to solitary cerebral amyloid angiopathy, Lewy body disease and the like. Furthermore, as diseases showing neurofibrillary tangles due to the PHF accumulation, examples include progressive supranuclear palsy, subacute sclerosing panencephalitic parkinsonism, postencephalitic parkinsonism, pugilistic encephalitis, Guam parkinsonism-dementia complex, Lewy body disease and the like.

The tau protein is generally composed of a group of related proteins that forms several bands at molecular weights of 48-65 kDa in SDS-polyacrylamide gel electrophoresis, and it promotes the formation of microtubules. It has been verified that tau protein incorporated in the PHF in the brain suffering from Alzheimer disease is abnormally phosphorylated compared with usual tau protein (J. Biochem., 99, 1807 (1986); Proc. Natl. Acad. Sci. USA, 83, 4913 (1986)). An enzyme catalyzing the abnormal phosphorylation has been isolated. The protein was named as tau protein kinase 1 (abbreviated as "TPK1" hereinafter in the specification), and its physicochemical properties have been elucidated (J. Biol. Chem., 267, 10897 (1992)). Moreover, cDNA of rat TPK1 was cloned from a rat cerebral cortex cDNA library based on a partial amino acid sequence of TPK1, and its nucleotide sequence was determined and an amino acid sequence was deduced. As a result, it has been revealed that the primary structure of the rat TPK1 corresponds to that of the enzyme known as rat GSK-3 β (glycogen synthase kinase 3β, FEBS Lett., 325, 167 (1993)).

It has been reported that A β, the main component of senile plaques, is neurotoxic (Science, 250, 279 (1990)). However, various theories have been proposed as for the reason why A β causes the cell death, and any authentic theory has not yet been established. Takashima et al. observed that the cell death was caused by A β treatment of fetal rat hippocampus primary culture system, and then found that the TPK1 activity was increased by Aβ treatment and the cell death by A β was inhibited by antisense of TPK1 (Proc. Natl. Acad. Sci. USA, 90, 7789 (1993); EP616032).

In view of the foregoing, compounds which inhibit the TPK1 activity may possibly suppress the neurotoxicity of A β and the formation of PHF and inhibit the nerve cell death in the Alzheimer disease, thereby cease or defer the progress of the disease.

As structurally similar compounds to the compounds of the present invention represented by formula (I) described later, the compounds disclosed in the International Publication Nos. WO01/70729, WO03/037888 and WO03/027080 are known. On the other hand, no pyrimidone derivative compounds that is substituted by fluorine-substituted pyrimidine at 6-position or by hydroxyl group at 5-position are known.

CITATION LIST

Patent Literature

EP616032
WO01/70729
WO03/037888
WO03/027080

Non Patent Literature

Biochem. Biophys. Res. Commun., 120, 885 (1984)
EMBO J., 4, 2757 (1985)
Proc. Natl. Acad. Sci. USA, 82, 4245 (1985)
Proc. Natl. Acad. Sci. USA, 85, 4506 (1988)
Neuron, 1, 827 (1988)
Nature, 375, 754 (1995)
Science, 269, 973 (1995)

Nature. 376, 775 (1995)
Neuron, 17, 1005 (1996)
Proc. Natl. Acad. Sci. USA, 94, 2025 (1997)
Society for Neuroscience Abstracts, 17, 1445 (1991)
The Journal of Neuroscience, 10, 2400 (1990)
J. Biochem., 99, 1807 (1986)
Proc. Natl. Acad. Sci. USA, 83, 4913 (1986)
J. Biol. Chem., 267, 10897 (1992)
FEBS Lett., 325, 167 (1993)
Science, 250, 279 (1990)
Proc. Natl. Acad. Sci. USA, 90, 7789 (1993)

SUMMARY OF INVENTION

Technical Problem

An object of the present invention is to provide a compound useful as an active ingredient of a medicament for preventive and/or therapeutic treatment of diseases such as Alzheimer disease, which has high clinical efficacy and can be administered with other medicament. More specifically, the object is to provide a novel compound useful as an active ingredient of a medicament that enables radical prevention and/or treatment of the neurodegenerative diseases such as Alzheimer disease by inhibiting the TPK1 activity to suppress the neurotoxicity of A β and the formation of the PHF and by inhibiting the death of nerve cells, which has high clinical efficacy and can be administered with other medicament.

Solution to Problem

In order to achieve the foregoing object, the inventors of the present invention conducted synthesis of compounds represented by the general formula (I) and screening their in vitro TPK1 inhibitory activities. As a result, they found that a novel compound represented by the following formula (I) had the desired activity. The present invention was achieved on the basis of these findings.

The present invention thus provides a compound represented by general formula (I):

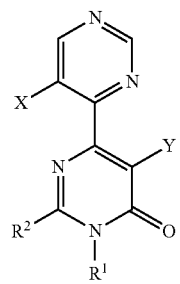
(I)

wherein X represents hydrogen atom or fluorine atom;
Y represents hydrogen atom or hydroxyl group, provided that when X represents hydrogen atom, Y is hydroxyl group;
$R^1$ represents a $C_{1-6}$ alkyl group; and
$R^2$ represents
a piperazin-1-yl group which may be substituted,
a piperidin-1-yl group which may be substituted,
a morpholin-4-yl group which may be substituted, or
a group represented by formula (ii):

(ii)

wherein $R^3$ represents hydrogen atom or a $C_{1-6}$ alkyl group;
$R^4$ represents a $C_{6-10}$ aryl group which may be substituted, or a $C_{6-10}$ aryl-CO— group which may be substituted; and
n represents an integer of 1 to 4.

Further, the present invention relates to a method for preparation of the above compound [I] or a pharmaceutically acceptable salt thereof.

Further, the present invention relates to a pharmaceutical composition containing the above compound [I] or a pharmaceutically acceptable salt thereof as an active ingredient.

Further, the present invention relates to a method for treatment or prophylaxis of a disease or condition, which comprises administering an effective amount of the above compound [I] or a pharmaceutically acceptable salt thereof to a patient.

Still further, the present invention relates to a use of the above compound [I] or a pharmaceutically acceptable salt thereof for manufacture of a medicament.

Still further, the present invention relates to a use of the above compound [I] or a pharmaceutically acceptable salt thereof for the inhibition of tau protein kinase 1 activity.

The desired compound [I] of the present invention or a pharmaceutically acceptable salt thereof exhibits an excellent inhibitory activity on TPK1. The pharmaceutical composition containing the compound of the present invention is useful as an active ingredient in a medicament for treatment or prophylaxis of a disease or condition which may be expected to be improved by inhibition of TPK1.

DESCRIPTION OF EMBODIMENTS

Unless otherwise indicated, the following definitions are set forth to illustrate and defined the meaning and scope of the various terms used to describe the invention herein.

The term "$C_1$-$C_6$ alkyl group" means an alkyl group having 1 to 6 carbon atoms which may be either linear or branched. The examples of $C_1$-$C_6$ alkyl group include methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, 1-ethylpropyl group, n-hexyl group, and isohexyl group. A $C_1$-$C_3$ alkyl moiety of the $C_1$-$C_3$ alky-O— group may be an alkyl group having 1 to 3 carbon atoms which may be either linear or branched. The examples of $C_1$-$C_3$ alkyl group include methyl group, ethyl group, n-propyl group, and isopropyl group.

The term "halogen atom" means fluorine atom, chlorine atom, bromine atom, or iodine atom.

The term "$C_6$-$C_{10}$ aryl group" means an aryl group having 6 to 10 carbon atoms. The examples of $C_6$-$C_{10}$ aryl group include phenyl group and naphthyl group. The bond position in the cycle is not limited.

The term "which may be substituted" means a group which may have one or more substituents. The number of substituents as well as their types and substituting positions are not particularly limited, and when two or more substituents are present, they may be the same or different.

As the $C_1$-$C_6$ alkyl group represented by $R^1$, methyl group is preferred.

As the $C_{1-6}$ alkyl group represented by $R^3$, methyl group is preferred.

As a $C_{6-10}$ aryl group in the $C_{6-10}$ aryl group which may be substituted, which is represented by $R^4$, phenyl group is preferred.

As a $C_{6-10}$ aryl-CO— group in the $C_{6-10}$ aryl-CO— group which may be substituted, which is represented by $R^4$, benzoyl group is preferred.

In the $C_{6-10}$ aryl group which may be substituted or the $C_{6-10}$ aryl-CO— group which may be substituted, which is represented by $R^4$, the $C_{6-10}$ aryl group or the $C_{6-10}$ aryl-CO— group may have one or more, preferably one or two substituents. Examples of the substituents include halogen atom, nitro group, cyano group and a $C_1$-$C_6$ alkyl-O— group. Among these substituents, halogen atom, nitro group or a $C_1$-$C_6$ alkyl-O— group is preferable.

The symbol "n" preferably represents 1 or 2.

An example of $R^2$ includes a group represented by formula (iii):

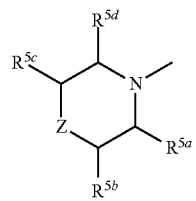

(iii)

wherein Z represents oxygen atom, $NR^{5e}$, or $CHR^{5f}$,
$R^{5a}$, $R^{5b}$, $R^{5c}$, $R^{5d}$, $R^{5e}$ and $R^{5f}$ each independently represents hydrogen atom, a $C_{1-6}$ alkyl group, or a $C_{6-10}$ aryl group. The above $C_{1-6}$ alkyl group represented by $R^{5a}$, $R^{5b}$, $R^{5c}$, $R^{5d}$, $R^{5e}$ or $R^{5f}$ may be substituted by a halogen atom. The above $C_{6-10}$ aryl group represented by $R^{5a}$, $R^{5b}$, $R^{5c}$, $R^{5d}$, $R^{5e}$ or $R^{5f}$ may have one or two substituents selected from the group consisting of a halogen atom, cyano group, nitro group, a $C_{1-6}$ alkyl group, a $C_{1-6}$ alkyl-O— group or a 5- or 6-membered monocyclic heterocyclic group. Of these substituents, halogen atom, cyano group, nitro group, a $C_{1-6}$ alkyl group, or a 5- or 6-membered monocyclic heterocyclic group are preferable, wherein the 5- or 6-membered monocyclic heterocyclic group may contain 1 to 3 hetero atoms selected from the group consisting of nitrogen atom and oxygen atom, and may be substituted by a $C_{1-6}$ alkyl group.

As the 5- or 6-membered monocyclic heterocyclic group as a substituent of the $C_{6-10}$ aryl group represented by $R^{5a}$, $R^{5b}$, $R^{5c}$, $R^{5d}$, $R^{5e}$ or $R^{5f}$, pyrrolidinyl group or 1,2,4-oxadiazolyl group is preferable and 1,2,4-oxadiazolyl group is more preferable.

As $R^{5a}$, $R^{5b}$ and $R^{5f}$, hydrogen atom is preferred.

As $R^{5c}$, a $C_{6-10}$ aryl group which may be substituted by a halogen atom, cyano group, or a 5- or 6-membered monocyclic heterocyclic group which may be substituted by a $C_{1-6}$ alkyl group is preferred.

As $R^{5d}$, hydrogen atom or a $C_{1-6}$ alkyl group which may be substituted by a halogen atom is preferred.

As $R^{5e}$, a $C_{6-10}$ aryl group which may have one or two substituents selected from the group consisting of a $C_{1-6}$ alkyl group is preferred.

A preferable examples of the compound represented by the formula (I) includes a compound wherein $R^2$ is a group represented by formula(iii) wherein
Z is oxygen atom,
$R^{5a}$, $R^{5b}$, and $R^{5d}$ are hydrogen atoms,
$R^{5c}$ is a $C_{6-10}$ aryl group which may be substituted by a halogen atom or a 5- or 6-membered monocyclic heterocyclic group. As explained above, the 5- or 6-membered monocyclic heterocyclic group may contain 1 to 3 hetero atoms selected from the group consisting of nitrogen atom and oxygen atom, and may be substituted by a $C_{1-6}$ alkyl group.

Among the preferable example, a more preferable example of the compound represented by the formula (I) includes the compound wherein X is hydrogen atom, Y is hydroxyl group and $R^{5c}$ is a phenyl group substituted by 1,2,4-oxadiazolyl which may be substituted by a $C_{1-6}$ alkyl group.

Preferable examples of the pyrimidone derivative of the present invention include:
(S)-5'-Fluoro-2-[2-(4-fluoro-phenyl)-morpholin-4-yl]-1-methyl-1H-[4,4']bipyrimidinyl-6-one,
(R)-5'-Fluoro-1-methyl-2-(3-methyl-morpholin-4-yl)-1H-[4,4']bipyrimidinyl-6-one,
(S)-5'-Fluoro-2-(3-fluoromethyl-morpholin-4-yl)-1-methyl-1H-[4,4']bipyrimidinyl-6-one,
(S)-5'-Fluoro-1-methyl-2-{2-[4-(5-methyl-[1,2,4]oxadiazol-3-yl)-phenyl]-morpholin-4yl}-1H-[4,4']bipyrimidinyl-6-one,
5'-Fluoro-1-methyl-2-[3-(4-pyrrolidin-1-yl-phenyl)-piperidin-1-yl]-1H-[4,4']bipyrimidinyl-6-one,
4-[4-(5'-Fluoro-1-methyl-6-oxo-1,6-dihydro-[4,4']bipyrimidinyl-2-yl)-piperazin-2yl]-benzonitrile,
2-[4-(2,3-Dimethyl-phenyl)-piperazin-1-yl]-5'-fluoro-1-methyl-1H-[4,4']bipyrimidinyl-6-one,
2-[2-(3,4-Dimethoxy-phenyl)-ethylamino]-5'-fluoro-1-methyl-1H-[4,4']bipyrimidinyl-6-one,
2-[2-(4-Chloro-phenyl)-2-oxo-ethylamino]-5'-fluoro-1-methyl-1H-[4, 4']bipyrimidinyl-6-one,
5'-Fluoro-1-methyl-2-{methyl-[2-(4-nitro-phenyl)-ethyl]-amino}-1H-[4,4']bipyrimidinyl-6-one, and
(S)-5-hydroxy-1-methyl-2-{2-[4-(5-methyl-1,2,4-oxadiazol-3-yl)phenyl]morpholin-4-yl}-1H-[4,4']bipyrimidinyl-6-one.

A pharmaceutically acceptable salt of any of the above compounds is also preferable.

The pharmaceutically acceptable salt of the compound represented by the aforementioned formula (I) may include the salt with inorganic acid such as hydrochloric acid, hydrobromic acid, sulfuric acid, phosphoric acid and the like and the salt with organic acid such as acetic acid, propionic acid, tartaric acid, fumaric acid, maleic acid, malic acid, oxalic acid, succinic acid, citric acid, benzoic acid, methanesulfonic acid, toluenesulfonic acid and the like.

In addition to the compound represented by the aforementioned formula (I), a pharmaceutically acceptable salt thereof, solvates thereof and hydrates thereof can also be used. The compound represented by the aforementioned formula (I) may have one or more asymmetric carbon atoms. As for the stereochemistry of such asymmetric carbon atoms, they may independently be in either (R) or (S) configuration, and the compound may exist as stereoisomers such as optical isomers, or diastereoisomers. Any stereoisomers of pure form, any mixtures of stereoisomers, racemates and the like fall within the scope of the present invention.

Examples of preferred compounds of the present invention are shown in the table 1 set out below. However, the scope of the present invention is not limited by the following compounds.

TABLE 1

| COMPOUND NO. | STRUCTURE |
| --- | --- |
| 1 | 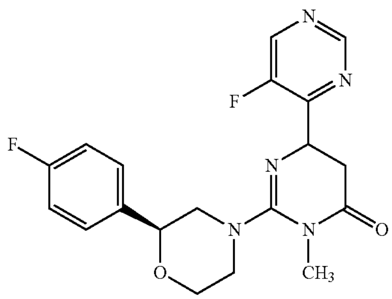 [SMILES: CN1C(=O)CC(c2ncncc2F)N=C1N1CCO[C@@H](c2ccc(F)cc2)C1] |
| 2 | 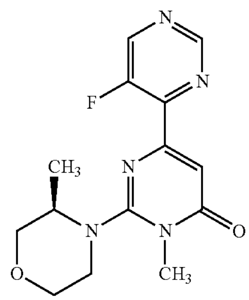 [SMILES: C[C@@H]1COCCN1c1nc(-c2ncncc2F)cc(=O)n1C] |
| 3 | 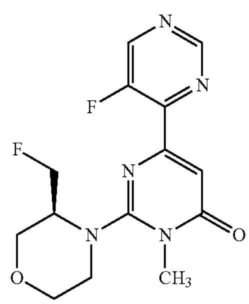 [SMILES: Cn1c(N2CCOC[C@H]2CF)nc(-c2ncncc2F)cc1=O] |
| 4 | 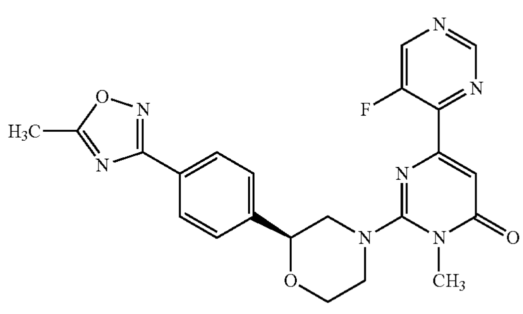 [SMILES: Cc1nc(-c2ccc([C@H]3CN(c4nc(-c5ncncc5F)cc(=O)n4C)CCO3)cc2)no1] |
| 5 | 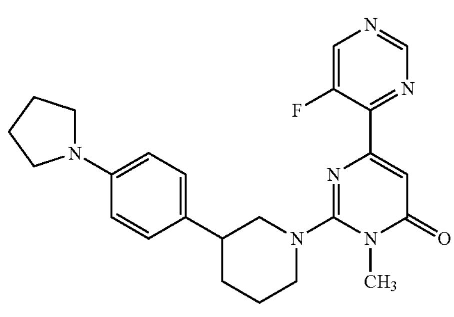 [SMILES: Cn1c(N2CCCC(c3ccc(N4CCCC4)cc3)C2)nc(-c2ncncc2F)cc1=O] |

TABLE 1-continued
| COMPOUND NO. | STRUCTURE |
| --- | --- |
| 6 | 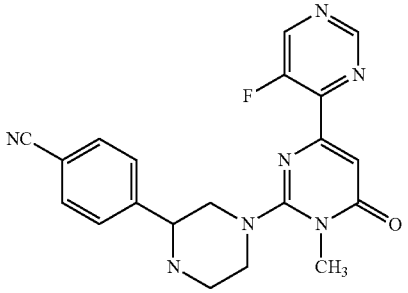 [SMILES: Cn1c(N2CCNC(c3ccc(C#N)cc3)C2)nc(-c2ncncc2F)cc1=O] |
| 7 | 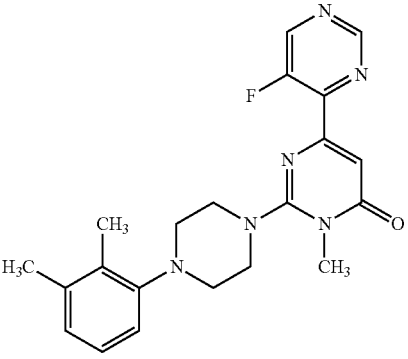 [SMILES: Cc1cccc(N2CCN(c3nc(-c4ncncc4F)cc(=O)n3C)CC2)c1C] |
| 8 | 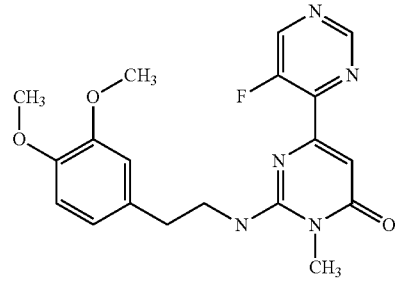 [SMILES: COc1ccc(CCNc2nc(-c3ncncc3F)cc(=O)n2C)cc1OC] |
| 9 | 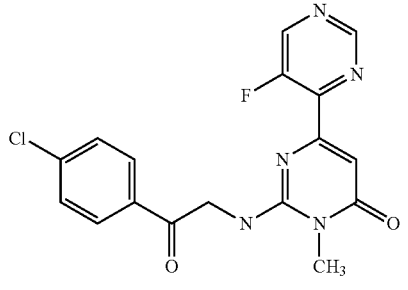 [SMILES: Cn1c(NCC(=O)c2ccc(Cl)cc2)nc(-c2ncncc2F)cc1=O] |
| 10 | 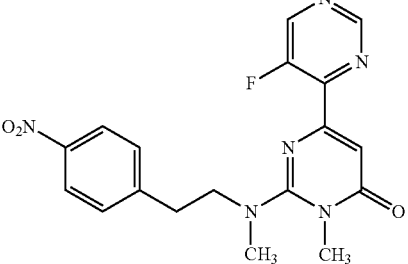 |

TABLE 1-continued

| COMPOUND NO. | STRUCTURE |
|---|---|
| 11 | 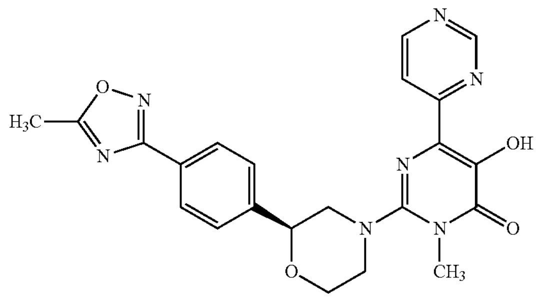 [SMILES: Cc1nc(-c2ccc([C@H]3CN(c4nc(-c5ccncn5)c(O)c(=O)n4C)CCO3)cc2)no1] |

The pyrimidone derivatives represented by the aforementioned formula (I) can be prepared, for example, according to the method explained below.

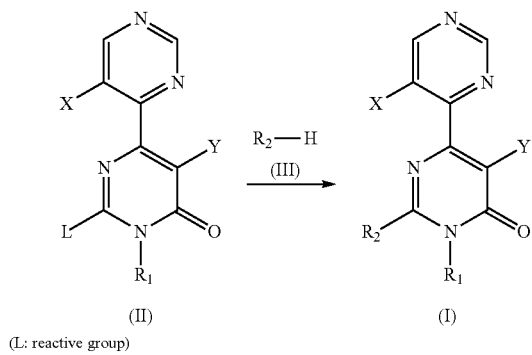

(L: reactive group)

The compound(II) can be prepared, for example, as described in the after-mentioned Reference example 1. Then the compound(II) is allowed to react with the formula (III) or salts thereof in the presence of a base such as sodium hydroxide, potassium hydroxide, sodium methoxide, sodium ethoxide, sodium carbonate, sodium hydrogencarbonate, potassium carbonate, triethylamine, diisopropylethylamine, N-ethylpiperidine, N-methylmorpholine and 1,8-diazabicyclo[5,4,0]undec-7-en for 1 to 100 hours at a suitable temperature ranging from 0° C. to 200° C. under nitrogen or argon atmosphere or under ordinary air to afford the desired compound(I).

Examples of a solvent for the reactions include, for example, alcoholic solvent such as methanol, ethanol, 1-propanol, isopropanol, tert-butanol, ethylene glycol, propylene glycol; etheric solvents such as diethyl ether, tert-butyl methyl ether, tetrahydrofuran, isopropyl ether; hydrocarbonic solvents such as benzene, toluene, xylene; halogenated hydrocarbonic solvents such as dichloromethane, chloroform, dichloroethane; aprotic polar solvents such as N,N-dimethylformamide, N,N-dimethylacetamide, N-methylpyrrolidone, dimethyl sulfoxide, sulfolane, hexamethylphosphoric triamide, water and the like. Generally, a single solvent or a mixture of two or more solvents may be used so as to be suitable to a base used.

TPK1 inhibitor may lead to the effective drug for the treatment of Alzheimer's disease and many structurally diverse classes of compounds with in vitro TPK1 inhibitory activity have been already disclosed. However, design of novel structures for the TPK1 inhibitor is expected to lead to clinically more efficient compounds through several improvements in in vitro and in vivo activities, kinase selectivity, ADME, PK/PD profiles and physical properties.

The compounds may also be possibly used as a medicament for therapeutic treatment of ischemic cerebrovascular accidents (Biochem J. 359, 1(2001)), traumatic head injury (Trends in Molecular Medicine 8, 126(2002)), Down syndrome, cerebral amyloid angiopathy, cerebral bleeding due to Lewy body disease and the like by suppressing the cytotoxicity of A β. Furthermore, the compounds may possibly be used as a medicament for therapeutic treatment of neurodegenerative diseases (Current Opinion in Neurobiology 12, 275(2002)) such as progressive supranuclear palsy (Acta Neuropathol. 104, 583(2002)), subacute sclerosing panencephalitic parkinsonism, postencephalitic parkinsonism, pugilistic encephalitis, Guam parkinsonism-dementia complex, Lewy body disease, Pick's disease (Acta Neuropathol. 104, 583(2002)), corticobasal degeneration (Acta Neuropathol. 104, 583(2002) frontotemporal dementia (Acta Neuropathol. 104, 583(2002)), vascular dementia, traumatic injuries, brain and spinal cord trauma, peripheral neuropathies, retinopathies and glaucoma and amyotrophic lateral sclerosis (European Journal of Neuroscience, Vol. 22, pp. 301-309, 2005) as well as other diseases such as non-insulin dependent diabetes (Biochem J. 359, 1(2001)), obesity, manic depressive illness and schizophrenia, alopecia.

In addition, inhibition of TPK1 could be useful in treating cancers, such as breast cancer, non-small lung carcinoma, thyroid cancer, T or B-cell leukaemia and several virus-induced tumours. For example, the active form of TPK1 has been shown to be elevated in the tumors of colorectral cancer patients and inhibition of TPK1 in colorectal cancer cells activates p53-dependent apoptosis and antagonises tumor growth.

Inhibitors of human TPK1 may also inhibit pfGSK3, an ortholog of this enzyme found in *Plasmodium falciparum*, as a consequence they could be used for the treatment of malaria (Biochimica et Biophysica Acta 1697, 181-196, 2004).

According to recent data, TPK1 inhibitors might be used in the treatment or prevention of *Pemphigus vulgaris*.

Accordingly, the compounds of the present invention are useful as an active ingredient of a medicament which radically enables preventive and/or therapeutic treatment of Alzheimer disease. In addition, the compounds of the present invention are also useful as an active ingredient of a medicament for preventive and/or therapeutic treatment of ischemic cerebrovascular accidents, Down syndrome, cerebral bleeding due to solitary cerebral amyloid angiopathy, progressive supranuclear palsy, subacute sclerosing panencephalitic parkinsonism, postencephalitic parkinsonism, pugilistic encephalosis, Guam parkinsonism-dementia complex, Lewy body disease, Pick's disease, corticobasal degeneration frontotemporal dementia, vascular dementia, traumatic injuries, brain and spinal cord trauma, peripheral neuropathies, retinopathies and glaucoma, non-insulin dependent diabetes, obesity, manic depressive illness, schizophrenia, alopecia, breast cancer, non-small cell lung carcinoma, thyroid cancer, T or B-cell leukemia, several virus-induced tumors, amyotrophic lateral sclerosis, malaria, pemphigus vulgaris and neutropenia induced by cancer chemotherapy.

Among the above exemplified diseases, the compounds of the present invention are particularly useful as an active ingredient of a medicament for preventive and/or therapeutic treatment of non-insulin dependent diabetes, Alzheimer's disease, ischemic cerebrovascular accidents, progressive supranuclear palsy, Pick's disease, corticobasal degeneration, frontotemporal dementia, traumatic injuries and brain and spinal cord trauma, amyotrophic lateral sclerosis and malaria. Among these diseases, Alzheimer's disease is more preferable.

As the compound of the present invention has good safety and good pharmacokinetics, the compound has preferable characteristics as a medicament.

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention, however, it is desirable to administer the medicament in a form of a pharmaceutical composition which comprises the aforementioned substance as an active ingredient and one or more of pharmaceutical additives. As the active ingredient of the medicament of the present invention, two or more of the aforementioned substance may be used in combination.

A type of the pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like. Injections or drip infusions may be prepared as powdery preparations such as in the from of lyophilized preparations, and may be used by dissolving just before use in an appropriate aqueous medium such as physiological saline. Sustained-release preparations such as those coated with a polymer may be directly administered intracerebrally.

Types of pharmaceutical additives used for the manufacture of the pharmaceutical composition, content rations of the pharmaceutical additives relative to the active ingredient, and methods for preparing the pharmaceutical composition may be appropriately chosen by those skilled in the art. Inorganic or organic substances, or solid or liquid substances may be used as pharmaceutical additives. Generally, the pharmaceutical additives may be incorporated in a ratio ranging from 1% by weight to 90% by weight based on the weight of an active ingredient.

Examples of excipients used for the preparation of solid pharmaceutical compositions include, for example, lactose, sucrose, starch, talc, cellulose, dextrin, kaolin, calcium carbonate and the like. For the preparation of liquid compositions for oral administrations, a conventional inert diluent such as water or a vegetable oil may be used. The liquid composition may contain, in addition to the inert diluent, auxiliaries such as moistening agents, suspension aids, sweeteners, aromatics, colorants, and preservatives. The liquid composition may be filled in capsules made of an absorbable material such as gelatin. Examples of solvents or suspension mediums used for the preparation of compositions for parenteral administration, e.g. injections, suppositories, include water, propylene glycol, polyethylene glycol, benzyl alcohol, ethyl oleate, lecithin and the like. Examples of base materials used for suppositories include, for example, cacao butter, emulsified cacao butter, lauric lipid, witepsol.

Dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 3000 mg (the weight of an active ingredient) to an adult.

EXAMPLES

The present invention will be explained more specifically with reference to examples. However, the scope of the present invention is not limited to the following examples. The compound number in the examples corresponds to that in the table above.

Preparation Example

Reference Example 1

Preparation of 2-chloro-5'-fluoro-1-methyl-1H-[4,4'] bipyrimidinyl-6-one

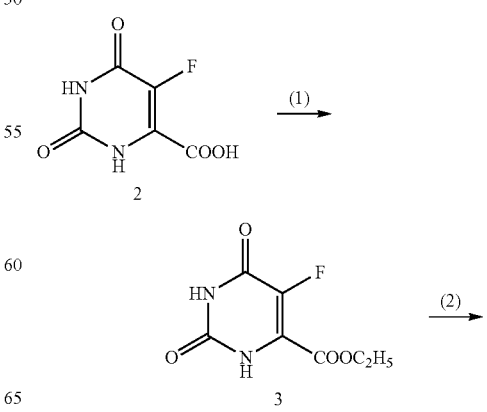

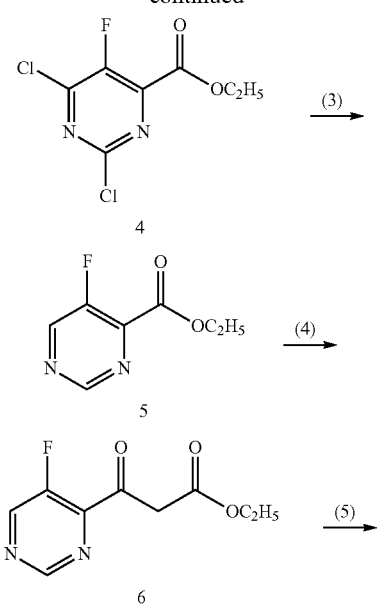

(5) 1,8-Diazabicyclo[5.4.0]undec-7-ene (7.96 g, 52.3 mmol) was added to a solution of ethyl 3-(5-fluoropyrimidin-4-yl)-3-oxo-propionate (intermediate 6, 11.1 g, 52.3 mmol),N-methylthiourea (9.43 g, 0.105 mol) in ethanol (33 ml) at 60° C., then mixture was stirred at 90° C. for 14 hours. The reaction mixture was added to 2% aqueous potassium bisulfate, and the resulting precipitate was collected by filtration, and washed with water and dried. The obtained precipitate was purified by silica-gel column chromatography (eluent; dichlorormethane/ethyl acetate = 20/1) to give 5′-fluoro-2-mercapto-1-methyl-1H-[4,4′]bipyrimidinyl-6-one (intermediate 7, 2.51 g, 20%).

(6) A suspension of 5′-Fluoro-2-mercapto-1-methyl-1H-[4,4′]bipyrimidinyl-6-one (intermediate 7, 2.51 g, 10.5 mmol) in a mixed solvent of dimethylformamide (7.5 ml) and 1,2-dichloroethane (7.5 ml) was added to phosphorus oxychloride (2.94 ml, 31.5 mmol) at 0° C., and the mixture was stirred at 40° C. for 60 minutes. The solution was poured into dichloromethane (100 ml), and the reaction mixture was added to saturated aqueous sodium bisulfate. The organic layer was washed with brine, dried over sodium sulfate, and concentrated in vacuo. The obtained residue was purified by silica-gel column chromatography (eluent; dichloromethane/ethyl acetate = 20/1) to give 2-chloro-5′-fluoro-1-methyl-1H-[4,4′]bipyrimidinyl-6-one (intermediate 1) as a brown solid (1.73 g, 68%).

Reference Example 2

Preparation of ethyl 3-oxo-3-(pyrimidin-4-yl)-2-{[2-(trimethylsilyl)ethoxy]methoxy}propanoate

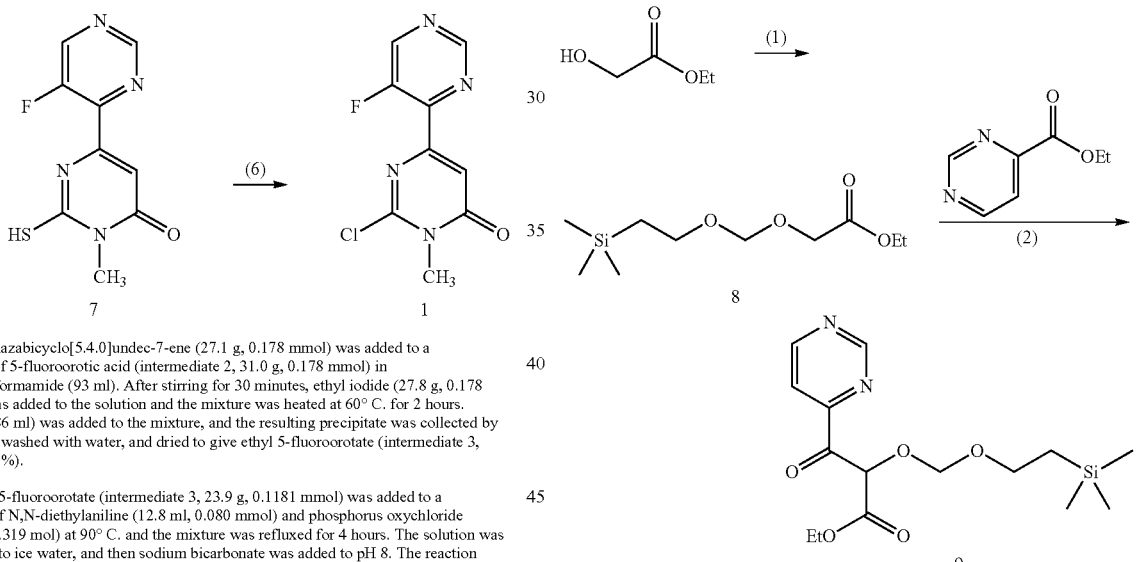

(1) To a mixture of ethyl 2-hydroxyacetate (2.00 g, 19.2 mmol) and N,N-diisopropylethylamine (2.73 ml, 21.1 mmol) in dichloromethane (50 ml) was added 2-(chloromethoxy)ethyltrimethysilane (3.52 g, 21.1 mmol) at room temperature. The mixture was stirred over night, and partitioned between water and dichloromethane. The organic layer was washes with brine, dried over sodium sulfate and concentrated in vacuo. The residue was purified by silica gel column chromatography (eluent; hexane/ethyl acetate = 93/7) to afford ethyl {[2-(trimethylsilyl)ethoxy]methoxy} acetate (intermediate 8) as a colorless oil (3.50 g, 14.9 mmol, 78%).

(2) To a solution of N,N-diisopropylamine (1.58 g, 15.6 mmol) in tetrahydrofuran (9.0 ml) was added dropwise 1.6 M-n-butyllithium solution in hexane (9.9 ml, 15.8 mmol) at -10° C. under nitrogen atmosphere. The mixture was warmed to room temperature, and stirred for 30 minutes. The mixture was cooled to -78° C., and ethyl {[2-(trimethylsilyl)ethoxy]methoxy}acetate ((intermediate 8, 3.50 g, 14.9 mmol) in tetrahydrofuran (9.0 ml) was slowly added at -78° C.. After 30 minutes, ethyl pyrimidine-4-carboxylate (2.07 g, 13.6 mmol; This compound was synthesized according to WO2007/011065) in tetrahydrofuran (9.0 ml) was added dropwise, and the mixture was stirred at -78° C. for 2 hours. The mixture was allowed to warm up to room temperature, and poured into saturated aqueous ammonium chloride. The organic layer was extracted with ethyl acetate, dried over sodium sulfate and concentrated in vacuo. The residue was purified by silica gel column chromatography (eluent; hexane/ethyl acetate = 75/25) to afford ethyl 3-oxo-3-pyrimidin-4-yl-2-{[2-(trimethylsilyl)ethoxy]methoxy}propanoate (intermediate 9) as a pale yellow oil (2.86 g, 8.40 mmol, 62%).

(1) 1,8-Diazabicyclo[5.4.0]undec-7-ene (27.1 g, 0.178 mmol) was added to a solution of 5-fluoroorotic acid (intermediate 2, 31.0 g, 0.178 mmol) in dimethylformamide (93 ml). After stirring for 30 minutes, ethyl iodide (27.8 g, 0.178 mmol) was added to the solution and the mixture was heated at 60° C. for 2 hours. Water (186 ml) was added to the mixture, and the resulting precipitate was collected by filtration, washed with water, and dried to give ethyl 5-fluoroorotate (intermediate 3, 23.9 g, 66%).

(2) Ethyl 5-fluoroorotate (intermediate 3, 23.9 g, 0.1181 mmol) was added to a mixture of N,N-diethylaniline (12.8 ml, 0.080 mmol) and phosphorus oxychloride (48.9 g, 0.319 mol) at 90° C. and the mixture was refluxed for 4 hours. The solution was poured into ice water, and then sodium bicarbonate was added to pH 8. The reaction mixture was extracted with ethyl acetate and washed with 5% aqueous potassium bisulfate, and brine. The organic layer was dried over sodium sulfate and concentrated in vacuo. The obtained residue was purified by silica-gel column chromatography (eluent; hexane/ethyl acetate = 4/1) to give ethyl 2,6-dichloro-5-fluoropyrimidine-4-carboxylate (intermediate 4, 26.1 g, 93%).

(3) Triethylamine (32.8 g, 0.324 mmol) was added to a solution of ethyl 2,6-dichloro-5-fluoropyrimidine-4-carboxylate (intermediate 4, 25.9 g, 0.108 mmol) in tetrahydrofuran (390 ml). 5% Palladium-carbon (5.2 g) was added and the mixture was stirred under a hydrogen atmosphere for 3 hours. The solid in the reaction system was removed by filtration, and the filtrate was extracted with ethyl acetate and washed with saturated aqueous sodium bicarbonate, and brine. The organic layer was dried over sodium sulfate and concentrated in vacuo. The obtained residue was purified by silica-gel column chromatography (eluent; hexane/ethyl acetate = 5/1) to give ethyl 5-fluoropyrimidine-4-carboxylate (intermediate 5, 11.8 g, 64%).

(4) A solution of lithium bis(trimethylsilyl)amide in hexane (1.05 mol/L, 75 ml) was added to a solution of ethyl acetate (8.67 g, 98.5 mmol) in tetrahydrofuran (200 ml) at -80° C.. After stirring the mixture for 40 minutes, a solution of ethyl 5-fluoropyrimidine-4-carboxylate (intermediate 5, 9.79 g) in tetrahydrofuran (200 ml) was added at -80° C. and the mixture was stirred for 3 hours at room temperature. The reaction mixture was added to 5% aqueous potassium bisulfate, and extracted with dichloromethane. The organic layer was washed with brine and dried over sodium sulfate. The solvent was evaporated under reduced pressure to give ethyl 3-(5-fluoropyrimidin-4-yl)-3-oxo-propionate (intermediate 6 (mixture of keto and enol form), 12.7 g, 99%).

Reference Example 3

Preparation of (S)-3-Fluoromethyl-morpholine hydrochloride (An Intermediate in a Preparation of Compound 3)

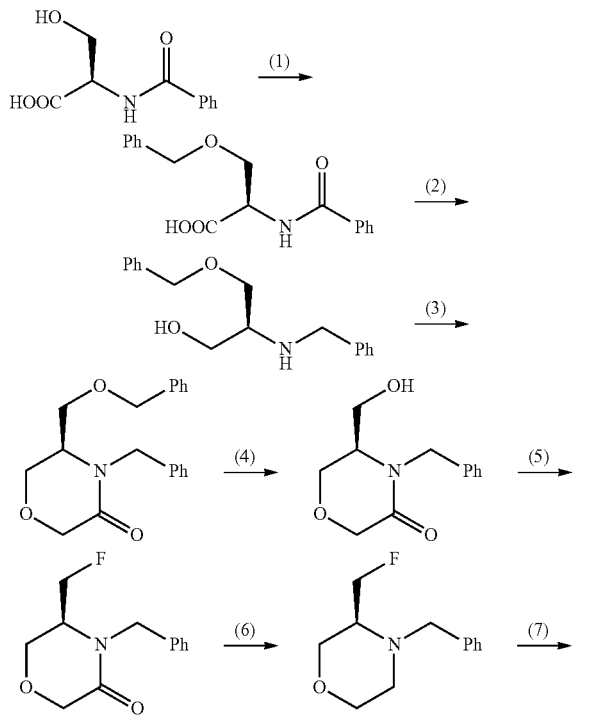

(1) To a ice-cooled suspension of sodium hydride (60% in mineral oil, 11.6 g, 290 mmol) in N,N-dimethylformamide (50 ml) under nitrogen atmosphere was added N-benzoyl-D-serine (20 g, 96 mmol) in N,N-dimethylformamide (50 ml) and stirred for one hour. Benzyl bromide (11.4 ml, d = 1.438, 96 mmol) was added to the solution ans stirred for 5 hours at room temperature. The resulting solution was poured into ice-water and washed with diethyl ether. After water phase was acidified by 4N hydrochloric acid, the solution was extracted by chloroform and organic phase was dried over sodium sulfate. Removal of the solvent under reduced pressure afforded crude N-benzoyl-O-benzyl-D-serine (33.3 g), which was used for the next step without further purification.

(2) To the solution of N-benzoyl-O-benzyl-D-serine in tetrahydrofuran (100 ml) was added 1M borane-tetrahydrofuran complex (1M in tetrahydrofuran solution, 500 ml, 500 mmol) at 0° C. under nitrogen atmosphere. The mixture was stirred at room temperature for 15 hours. After dropwise addition of methanol (100 ml), solvent was removed under reduced pressure. Methanol (200 ml) and 1N aqueous sodium hydroxide (300 ml) was added to the residue, and the solution was refluxed for 3 hours. After removal of methanol under reduced pressure, the solution was partitioned between water and ethyl acetate, and the organic layer was dried over sodium sulfate. Removal of the solvent afforded crude (S)-2-benzylamino-3-benzyloxy-1-ol (28.17 g) as a colorless oil, which was used for next step without further purification.

(3) To a solution of (S)-2-benzylamino-3-benzyloxy-propan-1-ol (28.17 g) in dichloromethane (300 ml) was added triethylamine (16.7 ml, d = 0.726, 12 mmol) and chloroacetyl chloride (9.6 ml, d = 1.418, 120 mmol) at 0° C., and the solution was stirred for one hour. The resulting solution was partitioned between 1N hydrochloric acid and dichloromethane. The organic layer was washed with brine, dried over sodium sulfate and concentrated in vacuo. The residue was dissolved into 2-propanol (200 ml), then potassium hydroxide (13 g, 200 mmol) was added. The mixture was stirred for 15 hours at room temperature and the solvent was removed under reduced pressure. The residue was partitioned between water and ethyl acetate. The organic layer was washed with brine, dried over sodium sulfate and concentrated in vacuo. The residue was purified by silica gel chromatography (eluent: hexane/ethyl acetate = 1/1) to afford (R)-4-benzyl-5-benzyloxymethyl-morpholin-3-one as a yellow oil (21.52 g, 72% from D-serine).

(4) A solution of (R)-4-benzyl-5-benzyloxymethyl-moropholin-3-one (23 g, 73.9 mmol), palladium on carbon (7.4 g) in ethanol (150 ml) and acetic acid (50 ml) was stirred under hydrogen atmosphere for 4 hours at 40° C.. Solvents was removed after filtration and following additional azeotropical removal of acetic acid with toluene twice afforded crude (R)-4-benzyl-5-hydroxymethyl-morpholin-3-one, which was used for next reaction without further purification.

(5) Bis(2-methoxyethyl)aminosulfur trifluoride (Deoxo-Fluor®, 75 g, 339 mmol) was added to a solution of (R)-4-benzyl-5-hydroxymethyl-morpholin-3-one in dichloromethane (50 ml) at room temperature and the solution was refluxed for 8 hours. After addition of methanol and water to the ice-cooled solution, the solution was partitioned between water and ethyl acetate, and the organic layer was dried over sodium sulfate. Solvent was removed under reduced pressure, and the residue was purified by silica gel column chromatography to afford (S)-4-benzyl-5-fluoromethyl-morpholin-3-one (13.6 g, 82%) as a yellow oil.

(6) Borane tetrahydrofuran complex solution (1.0 M in tetrahydrofuran, 200 ml) was added to a solution of (S)-4-benzyl-5-fluoromethyl-morpholin-3-one (13.6 g, 60.9 mmol) in tetrahydrofuran (100 ml) at 0° C. under nitrogen atmosphere, and the resulting solution was warmed to room temperature and stirred for 15 hours. Methanol was added to the solution dropwise, and the solvent was removed under reduced pressure. Methanol (150 ml) and 1M aqueous sodium hydroxide solution (150 ml) was added to the residue and the solution was refluxed for 3 hours. After removal of the solvent, the residue was partitioned between ethyl acetate and water, and the organic solvent was dried over sodium sulfate. Solvent was removed under reduced pressure and the residue was purified by silica gel column chromatography (eluent: hexane/ethyl acetate = 100/1 to 1/1) to afford (S)-4-benzyl-3-fluoromethyl-morpholine (6.5 g, 51%).

(7) To a solution of (S)-4-benzyl-3-fluoromethyl-morpholine (6.5 g, 31 mmol) in 1,2-dichloroethane (30 ml) was added 1-chloroethyl chloroformate (10 ml, d = 1.325, 92.7 mmol) at room temperature. The mixture was refluxed for 5 hours. The reaction mixture was cooled to room temperature and the methanol was added after the removal of 1,2-dichloroethane under reduced pressure. The mixture was refluxed for one hour and concentrated in vacuo. Addition of 2-propanol and concentration in vacuo was repeated twice, and the resulting solid was washed with ethyl acetate and filtered to afford (S)-3-fluoromethyl-morpholine hydrochloride (3.1 g, 65%) as a solid.

Example 1

Preparation of (S)-5'-fluoro-2-[2-(4-fluoro-phenyl)-morpholin-4-yl]-1-methyl-1H-[4,4']bipyrimidinyl-6-one (Compound 1)

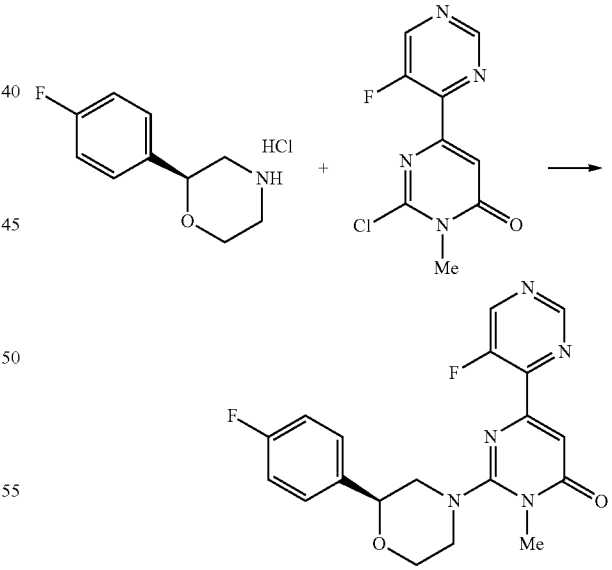

To a mixture of (S)-2-(4-fluorophenyl)-morpholine hydrochloride (0.19 g, 0.87 mmol; This compound was synthesized according to WO2007/011065) and 2-chloro-5'-fluoro-1-methyl-1H-[4,4']bipyrimidinyl-6-one (intermediate 1, 0.20 g, 0.83 mmol) in tetrahydrofuran (5 mL) was added triethylamine (0.35 mL, 2.5 mmol) at room temperature. The reaction mixture was stirred for 8 hours and poured into 1N hydrochloric acid. Extraction with chloroform was performed and the organic phase was dried over anhydrous sodium sulfate. The organic solvent was removed under reduced pressure and the residue was crystallized from ethanol to afford (S)-5'-fluoro-2-[2-(4-fluoro-phenyl)-morpholin-4-yl]-1-methyl-1H-[4,4']bipyrimidinyl-6-one (0.25 g, 0.65 mmol, 78%) as colorless crystalline.

Example 2

Preparation of (S)-5-hydroxy-1-methyl-2-{2-[4-(5-methyl-1,2,4-oxadiazol-3-yl)phenyl]morpholin-4-yl}-1H-[4,4']bipyrimidinyl-6-one (Compound 11)

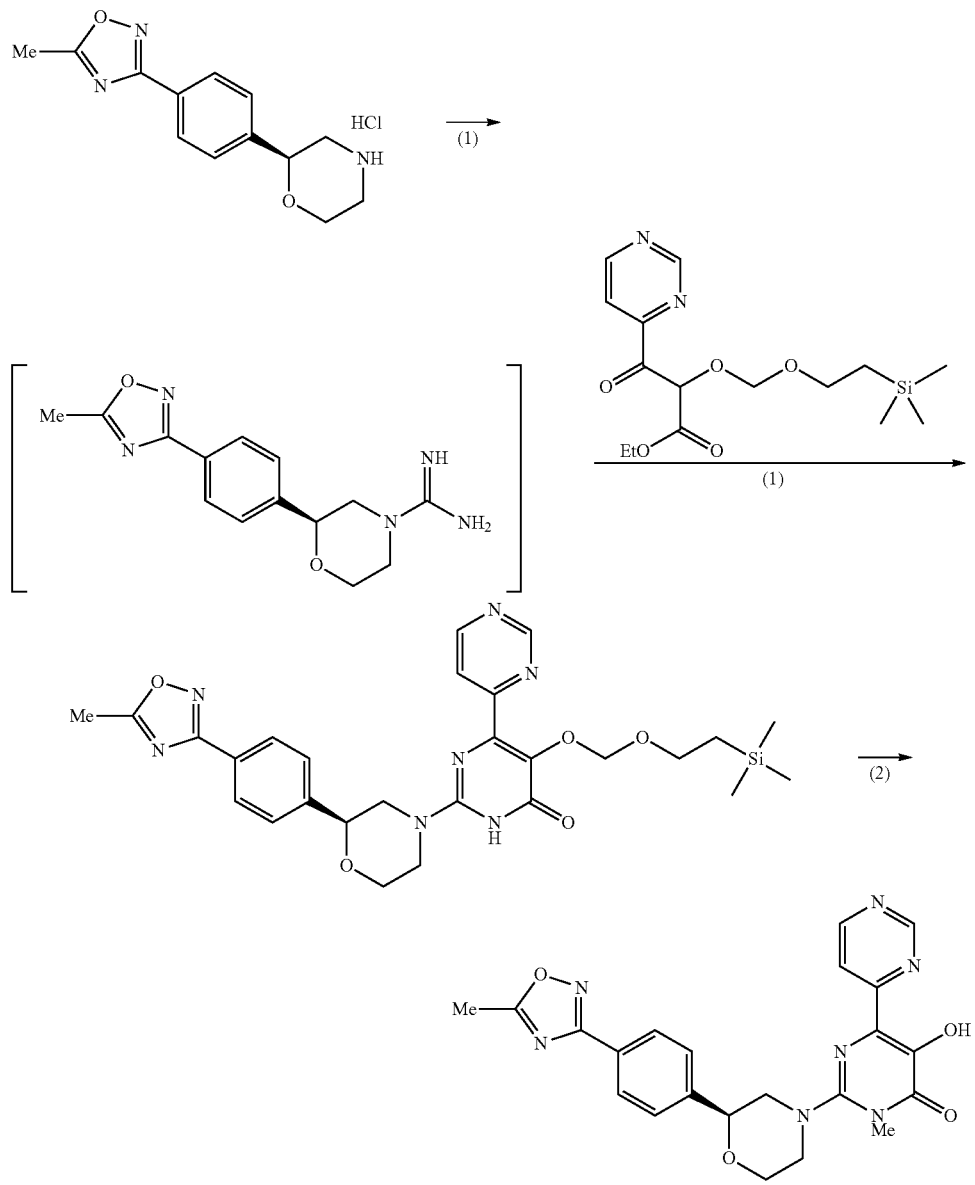

(1) (S)-2-{2-[4-(5-Methyl-1,2,4-oxadiazol-3-yl)phenyl]morpholin-4-yl}-5-{[2-(trimethylsily)ethoxy]methoxy}-1H-[4,4']bipyrimidinyl-6-one
To a mixture of (2S)-2-[4-(5-methyl-1,2,4-oxadiazol-3-yl)phenyl]morpholine hydrochloride (900 mg, 3.20 mmol; This compound was synthesized according to WO2008/078837) and 1H-pyrazole-1-carboxamidine hydrochloride (493 mg, 3.36 mmol) in N,N-dimethylformamide (2.0 ml) was added N,N-diisopropylethylamine (910 mg, 7.04 mmol) at room temperature, and stirred for 3 hours. Diethyl ether was added to the mixture, and the organic solvent was removed by decantation. The ethyl 3-oxo-3-pyrimidin-4-yl-2-{[2-(trimethylsilyl)ethoxy]methoxy}propanoate (intermediate 2, 1.64 g, 4.80 mmol), potassium carbonate (1.55 g, 11.2 mmol) and ethanol (4.0 ml) were added to the resulting solution. After refluxed for 10 hours, the mixture was poured into water. The organic compound was extracted with chloroform, dried over sodium sulfate and concentrated in vacuo. The residue was purified by silica gel column chromatography (eluent; chloroform/methanol = 98/2) to afford (S)-2-{2-[4-(5-methyl-1,2,4-oxadiazol-3-yl)phenyl]morpholin-4-yl}-5-{[2-(trimethylsilyl)ethoxy]methoxy}-1H-[4,4']bipyrimidinyl-6-one as a pale yellow solid (159 mg, 0.281 mmol, 9%).

(2) (S)-5-Hydroxy-1-methyl-2-{2-[4-(5-methyl-1,2,4-oxadiazol-3-yl)phenyl]morpholin-4-yl}-1H-[4,4']bipyrimidinyl-6-one
To a solution of (S)-2-{2-[4-(5-methyl-1,2,4-oxadiazol-3-yl)phenyl]morpholin-4-yl}-5-{[2-(trimethylsily)ethoxy]methoxy}-1H-[4,4']bipyrimidinyl-6-one (60 mg, 0.11 mmol) in acetonitrile (1.1 ml) was added hexamethyldisilazane (21 mg, 0.13 mmol) at room temperature. The mixture was refluxed for one hour, then (chloromethyl) dimethylchlorosilane (15 mg, 0.11 mmol) was added. The mixture was refluxed for 3 hours. After concentration under reduced pressure, the residue was dissolved into tetrahydrofuran (1.1 ml), and cesium fluoride (130 mg, 0.85 mmol) was added. The mixture was refluxed for 2 hours. The mixture was poured into saturated aqueous ammonium chloride, and extracted with chloroform. The organic layer was dried over sodium sulfate, and concentrated in vacuo. The residue was purified by silica gel column chromatography (eluent; chloroform/methanol = 99/1) to afford (S)-5-hydroxy-1-methyl-2-{2-[4-(5-methyl-1,2,4-oxadiazol-3-yl)phenyl]morpholin-4-yl}-1H-[4,4']bipyrimidinyl-6-one as a pale yellow solid (14 mg, 31 μmol, 29%).

The compounds in the following table were prepared in the same manner as the methods described above. The compound numbers in the following table correspond to those shown in the above described table of preferred compounds.

PHF formation, and that the medicaments of the present invention are effective for preventive and/or therapeutic treatment of Alzheimer disease and the above-mentioned diseases.

TABLE 2

| COMPOUND NO. | NMR | MS [M + 1] |
|---|---|---|
| 1 | 3.00-3.13 (1 H, m), 3.34 (1 H, t, J = 12.5 Hz), 3.48-3.61 (4 H, m), 3.69 (1 H, dd, J = 2.0, 13.3 Hz), 3.95 (1 H, t, J = 11.7 Hz), 4.13 (1 H, d, J = 12.1 Hz), 4.74 (1 H, d, J = 10.5 Hz), 7.02 (1 H, d, J = 1.6 Hz), 7.08 (2 H, td, J = 2.0, 8.6 Hz), 7.33-7.44 (2 H, m), 8.71 (1 H, t, J = 2.7 Hz), 9.10 (1 H, t, J = 2.3 Hz) (CDCl$_3$) | 386 |
| 2 | 1.21 (3 H, d, J = 6.6 Hz), 3.15 (1 H, dt, J = 3.2, 13.6 Hz), 3.36-3.42 (1 H, m), 3.43 (3 H, s), 3.47-3.55 (1 H, m), 3.67 (1 H, ddd, J = 2.9, 9.0, 11.51 Hz), 3.72-3.82 (3 H, m), 6.74 (1 H, d, J = 3.5 Hz), 9.03 (1 H, d, J = 3.5 Hz), 9.16 (1 H, d, J = 2.7 Hz) (DMSO-d6) | 306 |
| 3 | 3.42 (3 H, s), 3.33-3.35 (1 H, m), 3.47-3.57 (1 H, m), 3.62 (1 H, td, J = 2.3, 11.1 Hz), 3.75-3.89 (3 H, m), 4.05-4.18 (1 H, m), 4.64-4.80 (1 H, m), 4.80-4.96(1 H, m), 6.72 (1 H, s), 9.03 (1 H, d, J = 3.5 Hz), 9.16 (1 H, d, J = 2.7 Hz) (DMSO-d6) | 324 |
| 4 | 2.67 (3 H, s), 2.98 (1 H, dd, J = 10.5, 13.3 Hz), 3.13 - 3.26 (1 H, m), 3.48 (3 H, s), 3.70 (1 H, d, J = 12.9 Hz), 3.80 (1 H, d, J = 12.9 Hz), 3.89 (1 H, td, J = 2.2, 11.6 Hz), 4.07 (1 H, dd, J = 2.2, 11.5 Hz), 4.85 (1 H, dd, J = 2.0, 10.2 Hz), 6.76 (1 H, s), 7.62 (2 H, d, J = 8.2 Hz), 8.01 (2 H, d, J = 8.2 Hz), 9.02 (1 H, d, J = 3.5 Hz), 9.15 (1 H, d, J = 3.1 Hz) (DMSO-d6) | 450 |
| 5 | 1.62-1.83 (3 H, m), 1.94 (5 H, dt, J = 3.3, 6.3 Hz), 2.77-2.96 (3 H, m), 3.13-3.24 (4 H, m), 3.43 (3 H, s), 3.60-3.79 (2 H, m), 6.49 (2 H, d, J = 8.6 Hz), 6.67 (1 H, s), 7.10 (2 H, d, J = 8.6 Hz), 9.00 (1 H, d, J = 3.5 Hz), 9.14 (1 H, d, J = 3.1 Hz) (DMSO-d6) | 435 |
| 6 | 3.45 (3 H, s), 3.47-3.52 (2 H, m), 3.52-3.60 (1 H, m), 3.61-3.70 (1 H, m), 3.85-3.91 (2 H, m), 4.77 (1 H, t, J = 10.1 Hz), 6.83 (1 H, s), 7.91-7.94 (3 H, m), 7.99-8.02 (1 H, m), 9.05 (1 H, d, J = 3.9 Hz), 9.18 (1 H, d, J = 2.7 Hz), 10.01 (1 H, d, J = 9.0 Hz), 10.46 (1 H, d, J = 9.8 Hz) (DMSO-d6) | 392 |
| 7 | 2.20 (3 H, s), 2.22 (3 H, s), 2.96 (4 H, t, J = 4.5 Hz), 3.47 (7 H, br), 6.73 (1 H, s), 6.91 (1 H, d, J = 7.4 Hz), 6.94 (1 H, d, J = 7.8 Hz), 7.06 (1 H, t, J = 7.6 Hz), 9.03 (1 H, d, J = 3.5 Hz), 9.16 (1 H, d, J = 2.7 Hz) (DMSO-d6) | 395 |
| 8 | 2.83-2.88 (2 H, m), 3.30 (3 H, s), 3.53-3.60 (2 H, m), 3.71 (3 H, s), 3.73 (3 H, s), 6.41 (1 H, s), 6.74 (1 H, dd, J = 8.2, 2.0 Hz), 6.82 (1 H, d, J = 2.0 Hz), 6.86 (1 H, d, J = 8.2 Hz), 7.57 (1 H, t, J = 5.3 Hz), 9.02 (1 H, d, J = 3.5 Hz), 9.13 (1 H, d, J = 2.7 Hz) (DMSO-d6) | 386 |
| 9 | 3.43 (3 H, s), 4.87 (2 H, d, J = 5.5 Hz), 6.43 (1 H, s), 7.61-7.65 (2 H, m), 7.93 (1 H, t, J = 5.5 Hz), 8.01-8.08 (2 H, m), 8.84 (1 H, d, J = 3.5 Hz), 9.05 (1 H, d, J = 2.7 Hz) (DMSO-d6) | 374 |
| 10 | 2.99 (3 H, s), 3.12 (2 H, t, J = 7.2 Hz), 3.31 (3 H, s), 3.63 (2 H, t, J = 7.2 Hz), 6.57 (1 H, s), 7.54-7.58 (2 H, m), 8.10-8.14 (2 H, m), 9.03 (1 H, d, J = 3.5 Hz), 9.15 (1 H, d, J = 2.7 Hz) (DMSO-d6) | 385 |
| 11 | 2.67 (3 H, s), 3.05 (1 H, dd, J = 10.2, 12.5 Hz), 3.17 (1 H, dt, J = 3.1, 12.5 Hz), 3.33 (1 H, d, J = 13.3 Hz), 3.43-3.48 (1 H, m), 3.67 (3 H, s), 4.03 (1 H, dt, J = 2.4, 11.7 Hz), 4.21 (1 H, d, J = 2.4, 11.7 Hz), 4.80 (1 H, dd, J = 2.4, 11.0 Hz), 7.55 (2 H, d, J = 7.8 Hz), 8.11 (2 H, d, J = 7.8 Hz), 8.15 (1 H, dd, J = 1.6, 5.5 Hz), 8.89 (1 H, d, J =5.5 Hz), 9.21 (1 H, d, J = 1.6 Hz), 12.95 (1 H, s) (CDCl$_3$) | 448 |

Experiment 1: Inhibitory Activity of the Medicament of the Present Invention Against P-GS1 Phosphorylation by Bovine Cerebral TPK1

A mixture containing 100 mM MES-sodium hydroxide (pH 6.5), 1 mM magnesium acetate, 0.5 mM EGTA, 5 mM β-mercaptoethanol, 0.02% Tween 20, 10% glycerol, 12 µg/ml P-GS1, 41.7 µM [γ$^{-32}$P] ATP (68 kBq/ml), bovine cerebral TPK1 and a compound shown in Table (a final mixture contained 1.7% DMSO deriving from a solution of a test compound prepared in the presence of 10% DMSO) was used as a reaction system. The phosphorylation was started by adding ATP, and the reaction was conducted at 25° C. for 2 hours, and then stopped by adding 21% perchloric acid on ice cooling. The reaction mixture was centrifuged at 12,000 rpm for 5 minutes and adsorbed on P81 paper (Whatmann), and then the paper was washed four times with 75 mM phosphoric acid, three times with water and once with acetone. The paper was dried, and the residual radioactivity was measured using a liquid scintillation counter. The results are shown in the table below. The test compound markedly inhibited the P-GS1 phosphorylation by TPK1. The results strongly suggest that the medicaments of the present invention inhibit the TPK1 activity, thereby suppress the A β neurotoxicity and the

TABLE 3

| COMPOUND NO. | IC50/nM |
|---|---|
| 1 | 15.5 |
| 2 | 19.7 |
| 3 | 33.4 |
| 4 | 8.4 |
| 5 | 33.1 |
| 6 | 10.1 |
| 7 | 78.3 |
| 8 | 75.3 |
| 9 | 607.9 |
| 10 | 164.8 |
| 11 | 6.7 |

Experiment 2: Inhibitory Activity on Tau Phosphorylation In Vivo

Test compound was administrated to male CD-1 mice of 5-6 weeks weighing 25-35 g (Charles River Japan, inc.) at 1, 3, 10, 30 mg/kg p.o. (0.5% Tween/H$_2$O suspension) and after one hour, mice were decapitated and cortex was promptly removed, followed by being frozen in liquid N$_2$. Cortex was directly homogenized with 2.3% SDS homogenization buffer (62.5 mM Tris-HCl, 2.3% SDS, 1 mM each of EDTA, EGTA and DTT, protease inhibitor cocktail (sigma P2714) containing 0.2 μM 4-(2-Aminoethyl)benzenesulfonyl fluoride (AEBSF), 13 μM bestatin, 1.4 μM E-64, 0.1 mM leupeptin, 30 nM aprotinin, pH 6.8) and centrifuged at 15000×g for 15 min at 4° C. Protein concentrations were determined using DC protein assay kit (BIO-RAD). Supernatants were diluted with sample buffer (62.5 mM Tris-HCl, 25% glycerol, 2% SDS, 0.01% Bromophenol Blue, pH6.8) to adjust the protein concentrations around 0.5-2 mg/mg and then boiled for 5 min. 10 μg of samples were applied on 10% SDS-PAGE mini slab gels and transferred onto PVDF membranes. Membranes were incubated with PBS containing 5% non-fat milk for one hour at room temperature and then probed with pS396 anti-body (BIOSOURCE) overnight at 4° C. Anti-rabbit IgG HRP-conjugated anti-body (Promega) was used as secondary antibody. Membranes were visualized by ECL kit (Amerasham Bioscience) and detected by LAS1000 (Fuji Photo Film).

INDUSTRIAL APPLICABILITY

The compounds of the present invention have TPK1 inhibitory activity and are useful as an active ingredient of a medicament for preventive and/or therapeutic treatment of diseases caused by abnormal advance of TPK1 such as neurodegenerative diseases (e.g. Alzheimer disease) and the above-mentioned diseases.

The invention claimed is:

1. A compound represented by general formula (I)

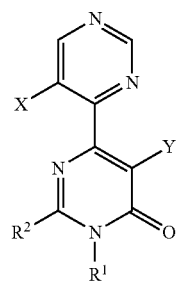

(I)

wherein X represents a hydrogen atom;

Y represents a hydroxyl group;

$R^1$ represents a $C_{1-6}$ alkyl group; and $R^2$ is a group represented by the following formula (iii):

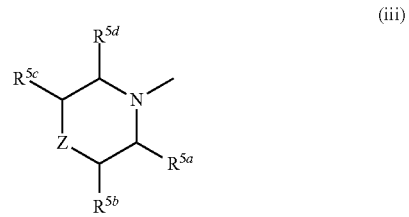

(iii)

wherein Z represents an oxygen atom;

$R^{5a}$, $R^{5b}$, and $R^{5d}$ each independently represents a hydrogen atom; and $R^{5c}$ represents a phenyl group substituted by 1,2,4-oxadiazolyl which may be substituted by a $C_{1-6}$ alkyl group, or a pharmaceutically acceptable salt thereof.

2. The compound according to claim 1, which is (S)-5-hydroxy-1-methyl-2-{2-[4-(5-methyl-1,2,4-oxadiazol-3-yl)phenyl]morpholin-4-yl}-1H-[4,4']bipyrimidinyl-6-one, or a pharmaceutically acceptable salt thereof.

3. A method for therapeutic treatment of a disease or condition selected from the group consisting of non-insulin dependent diabetes, Alzheimer's disease, ischemic cerebrovascular accidents, progressive supranuclear palsy, Pick's disease, corticobasal degeneration, and frontotemporal dementia, which comprises administering to a patient in need thereof an effective amount of the compound according to claim 1.

4. The method according to claim 3, wherein the disease or condition is Alzheimer's disease.

5. A pharmaceutical composition for inhibiting tau protein kinase 1 activity, comprising the compound according to claim 1 as an active ingredient.

* * * * *